United States Patent [19]

Imai et al.

[11] 4,370,257

[45] Jan. 25, 1983

[54] CATALYST COMPONENT FOR POLYMERIZATION OF ALPHA-OLEFINS AND METHOD FOR USING THE SAME

[75] Inventors: Masafumi Imai, Ooi; Hiroshi Ueno, Namekawa; Naomi Inaba, Ooi; Makoto Yoda, Kawagoe; Shozo Wada, Zushi, all of Japan

[73] Assignee: Toa Nenryo Kogyo Kabushiki Kaisha, Tokyo, Japan

[21] Appl. No.: 177,024

[22] Filed: Aug. 11, 1980

[30] Foreign Application Priority Data

Aug. 30, 1979 [JP] Japan .................. 54-109681

[51] Int. Cl.$^3$ ............................ C08F 4/02; C08F 4/64
[52] U.S. Cl. ............................ 252/429 B; 252/431 R; 252/431 C; 252/431 N; 252/431 P; 526/125; 568/700; 568/715; 568/716; 568/821; 568/822; 568/832; 568/851
[58] Field of Search ........... 252/429 B, 431 R, 431 C, 252/431 N, 431 P

[56] References Cited

U.S. PATENT DOCUMENTS 3,381,047  4/1968  Eleuterio et al. .......... 252/429 B X
3,784,481  1/1974  Lassau et al. ............. 252/429 B X
4,220,554  9/1980  Scata et al. ............... 252/429 B
4,232,139  11/1980 Minami et al. ............ 252/429 B X Primary Examiner—Patrick Garvin
Attorney, Agent, or Firm—M. B. Kurtzman

[57] ABSTRACT

A process for producing a magnesium containing support for titanium comprising contacting magnesium metal, a halogenated hydrocarbon and a compound represented by the formula $X'_mC(OR')_{4-m}$ wherein $X'$ is a hydrogen atom, a halogen atom or a $C_1$–$C_{10}$ alkyl, aryl, cycloalkyl or halogenated alkyl, aryl, cycloalkyl group, $R'$ is a $C_1$–$C_{20}$ alkyl, aryl or cycloalkyl group and m is 0, 1 or 2 to form a magnesium-containing solid represented by the formula $R'OMgX$ and thereafter contacting the magnesium-containing solid with a Lewis base or a compound which can form an ester such as benzoyl chloride and a titanium compound such as titanium tetrachloride. The obtained magnesium supported titanium composition is useful as a catalyst component in combination with a co-catalyst organoaluminum compound for the polymerization of olefins.

14 Claims, No Drawings

CATALYST COMPONENT FOR POLYMERIZATION OF ALPHA-OLEFINS AND METHOD FOR USING THE SAME

BACKGROUND OF THE INVENTION

This invention relates to a catalyst component for polymerization of alpha-olefins and a method for using the same. More specifically, this invention relates to a carrier-supported titanium catalyst component which exhibits high activity and high stereospecificity and which can produce polymers having a uniform particle diameter and to a process for using the same.

In the production of olefin polymers, especially polypropylene, using Ziegler-Natta type catalysts, many attempts have been made heretofore to obtain catalysts exhibiting high activity and high stereospecificity for the ultimate purpose of offering the resulting polymers as final products without any further treatment.

In recent years, supported catalysts comprising titanium supported on various carriers, particularly magnesium compounds have been developed. These supported catalysts greatly increase the polymerization ability of the titanium component as compared with conventional Ziegler-Natta type catalysts. However, no ultimate catalyst has yet been perfected.

Attempts have been made to obtain catalysts capable of controlling the particle size of the resulting polymer while retaining their high activity and high stereospecificity.

It is said that the shape of a polymer obtained by using a Ziegler-Natta type catalyst is generally affected by the shape of the catalyst component used. With respect to supported catalysts there are few methods available for controlling shape.

As far as supported catalysts having a magnesium compound, particularly magnesium chloride, as a carrier are concerned, there has been known, for example, a method which comprises spray-drying molten magnesium chloride to form spherical particles, and supporting titanium tetrachloride thereon in the suspended state [(1) Japanese Laid-Open Patent Publication No. 65999/74, (2) Japanese Laid-Open Patent Publication No. 38590/77], and a method which comprises supporting titanium tetrachloride on classified powdery magnesium chloride in the suspended state [(3) Japanese Laid-Open Patent Publication No. 127185/76].

The catalysts obtained by the methods (1) and (2) relate mainly to the case of producing polyethylene. These catalysts exhibit low stereospecificity when used for producing polypropylene. Method (3) relates mainly to a catalyst for the polymerization of ethylene. The particle characteristics of the resulting polymer are good, but the polymerization efficiency of the catalyst is not necessarily high.

The specification of Japanese Laid-Open Patent Publication No. 146292/78 describes a method which comprises reacting metallic magnesium and an organic halide or an organic compound of magnesium with an ortho-silicic acid ester to form a magnesium compound having controlled particle characteristics, treating this compound with an electron donor compound and/or a halogen compound to obtain a substance containing a magnesium halide, especially magnesium chloride, as a main ingredient, and supporting titanium tetrachloride on this substance. Although the particle size distribution of the resulting polymer is considerably improved, the activity and stereospecificity of the catalyst are never high and the method cannot be said to be economically advantageous because the ortho-silicic acid ester, which is essential in this method, is a special compound and is difficult to obtain.

SUMMARY OF THE INVENTION

The present inventors continued extensive investigations in order to provide a catalyst component which exhibits high activity and high stereospecificity and can produce free-flowing polyolefins, especially polypropylene, having a narrow particle size distribution and a low content of fine powder. These investigations have led to the present invention.

The gist of the present invention resides in a catalyst component for polymerization of alpha-olefins which is prepared by contacting:

(1) a magnesium-containing solid obtained by contacting (a) metallic magnesium, (b) a halogenated hydrocarbon expressed by the general formula RX, wherein R is a $C_1$–$C_{20}$ alkyl, aryl or cycloalkyl group and X is a halogen atom, and (c) a compound of the general formula $X'_m C(OR')_{4-m}$, wherein $X'$ is a hydrogen atom, or a $C_1$–$C_{10}$ alkyl, aryl or cycloalkyl group; $R'$ is a $C_1$–$C_{20}$ alkyl, aryl or cycloalkyl group and m is 0, 1 or 2;

(2) a titanium compound; and (3) an electron donor compound;

and a process for polymerizing alpha-olefins which comprises homopolymerizing an alpha-olefin or copolymerizing it with ethylene or another alpha-olefin in the presence of catalyst formed of said catalyst component and an organoaluminum compound.

DETAILED DESCRIPTION OF THE INVENTION

Metallic magnesium may be any, but is suitably in the form of a powder or chips in particular. Desirably, such metallic magnesium is washed, prior to use, with an inert hydrocarbon, for example, a saturated aliphatic, alicyclic or aromatic hydrocarbon having 6 to 8 carbon atoms, and dried under heat in the presence of an inert gas such as nitrogen.

Preferred halogenated hydrocarbons expressed by the general formula RX are those in which R is a $C_1$–$C_{20}$, preferably $C_1$–$C_8$, alkyl, aryl or cycloalkyl group and X is chlorine or bromine. Illustrative examples of the halogenated hydrocarbons are methyl, ethyl, isopropyl, n-butyl, n-octyl and cyclohexyl chlorides and bromides, chlorobenzene, o-chlorotoluene and the like.

Instead of using metallic magnesium and the halogenated hydrocarbon, a compound obtained by contacting these compounds in advance may be used. Typical examples of such a compound are the Grignard reagents. Illustrative examples of the Grignard reagents are $ClMgCH_3$, $ClMgC_2H_5$, $ClMgC_3H_7$, $ClMgC_4H_9$, $ClMgi\text{-}C_4H_9$, $ClMgC_6H_{13}$, $ClMgC_8H_{17}$, $BrMgC_2H_5$, $BrMgC_4H_9$, $BrMgi\text{-}C_4H_9$, $IMgC_4H_9$, $ClMgC_6H_5$ and $BrMgC_6H_5$.

The compounds expressed by the general formula $X'_m C(OR')_{4-m}$ (to be abbreviated simply as alkoxy compounds) are those in which $X'$ is selected from a hydrogen atom, a halogen atom or $C_1$–$C_{10}$ alkyl, aryl or cycloalkyl group, $R'$ is selected from $C_1$–$C_{20}$ alkyl, aryl or cycloalkyl group and m is selected from 0, 1 or 2. Illustrative examples of the above compounds in which m is 0, 1 and 2 are given below.

As the compounds in which m is 0, i.e., ortho-carbonic acid esters, there can be cited methyl ortho-carbonate [$C(OCH_3)_4$], ethyl ortho-carbonate [$C(OC_2H_5)_4$], propyl ortho-carbonate [$C(OC_3H_7)_4$], butyl ortho-carbonate [$C(OC_4H_9)_4$], isobutyl ortho-carbonate [$C(O-i-C_4H_9)_4$], hexyl ortho-carbonate [$O(OC_6H_{13})_4$], octyl ortho-carbonate [$C(OC_8H_{17})_4$], and the like.

Examples of the compounds in which m is 1, i.e., ortho-formic acid esters and the substitution products thereof, include methyl ortho-formate [$HC(OCH_3)_3$], ethyl ortho-formate [$HC(OC_2H_5)_3$], propyl ortho-formate [$HC(OC_3H_7)_3$], butyl ortho-formate [$HC(OC_4H_9)_3$], isobutyl ortho-formate [$HC(O-i-C_4H_9)_3$], hexyl ortho-formate [$HC(OC_6H_{13})_3$], octyl ortho-formate [$HC(OC_8H_{17})_3$], and phenyl ortho-formate [$HC(OC_6H_5)_3$] which correspond to X' being a hydrogen atom; methyl ortho-acetate [$CH_3C(OCH_3)_3$], ethyl ortho-acetate [$CH_3C(OC_2H_5)_3$], methyl ortho-propionate [$CH_3CH_2C(OCH_3)_3$], ethyl ortho-propionate [$CH_3CH_2C(OC_2H_5)_3$], $C_6H_{11}C(OC_2H_5)_3$, $C_6H_5C(OC_2H_5)_3$, $C_7H_8C(OC_2H_5)_3$ and $C_8H_{11}C(OC_2H_5)_3$ which correspond to X' being an alkyl, cycloalkyl or aryl group; ethyl ortho-bromoacetate [$CH_2BrC(OC_2H_5)_3$], ethyl ortho-chloroacetate [$CH_2ClC(OC_2H_4)_3$], ethyl ortho-alpha-bromopropionate [$CH_3CHBrC(OC_2H_5)_3$] and ethyl ortho-alpha-chloropropionate [$CH_3CHClC(OC_2H_5)_3$], which result from substitution of a halogen atom for the hydrogen atom of the alkyl group; and methyl ortho-chloroformate [$ClC(OCH_3)_3$], ethyl ortho-chloroformate [$ClC(OC_2H_5)_3$], propyl ortho-chloroformate [$ClC(OC_3H_7)_3$], isobutyl ortho-chloroformate [$ClC(O-i-C_4H_9)_3$], octyl ortho-chloroformate [$ClC(OC_8H_{17})_3$], phenyl ortho-chloroformate [$ClC(OC_6H_5)_3$] and ethyl orthobromoformate [$BrC(OC_2H_5)_3$] which correspond to X' being a halogen atom. Of these, the ortho-formic acid esters corresponding to X' being H, especially those in which R' is an alkyl group having 1 to 8 carbon atoms, such as methyl ortho-formate, ethyl ortho-formate, butyl ortho-formate and octyl ortho-formate, are desirable.

Examples of the compounds in which m is 2, i.e., compounds of formula $X'_2C(OR')_2$, include ethylidene dimethyl ether [$CH_3CH(OCH_3)_2$], ethylidene diethyl ether [$CH_3CH(OC_2H_5)_2$], methylene [$CH_2(OCH_3)_2$], methylene diethyl ether [$CH_2(OC_2H_5)_2$], monochloroacetal [$CH_2ClCH(OC_2H_5)_2$, dichloroacetal [$CHCl_2CH(OC_2H_5)_2$], trichloroacetal [$CCl_3CH(OC_2H_5)_2$], monobromoacetal [$CH_2BrCH(OC_2H_5)_2$], monoiodoacetal [$CH_2ICH(OC_2H_5)_2$] and benzaldehyde diethyl acetal [$C_6H_5CH(OC_2H_5)_2$].

Among the above compounds, the ortho-formic acid esters, especially the alkyl esters with 1 to 8 carbon atoms such as methyl ortho-formate, ethyl ortho-formate and butyl ortho-formate, are especially suitable.

The aforesaid magnesium-containing solid is obtained by contacting the alkoxy compound with metallic magnesium and the halogenated hydrocarbon. The method of contacting the alkoxy compound with metallic magnesium and halogenated hydrocarbon is not particularly limited, and any method can be used. For example, the three may be contacted simultaneously. Or as stated hereinabove, it is possible to contact metallic magnesium with the halogenated hydrocarbon in advance to form a so-called Grignard reagent, and then to contact it with the alkoxy compound. However, a method which comprises adding a solution of the halogenated hydrocarbon to a suspension of metallic magnesium in a solution of the aforesaid alkoxy compound, and thus contacting them with each other is especially desirable. These reactions by contacting may be carried out in the presence of a similar inert hydrocarbon to those described hereinabove with regard to metallic magnesium.

Furthermore, for the purpose of promoting these reactions, iodine, alkyl iodides, or inorganic halides such as calcium chloride, copper chloride, manganese chloride or hydrogen halides may be used.

The contacting reaction may be carried out at 40° to 250° C., desirably 60° to 120° C., for 1 to 10 hours.

The proportions of the aforesaid alkoxy compound and metallic magnesium are desirably such that the proportion of the OR' group in the alkoxy compound is at least 1, especially 3 to 5 per atom of magnesium as the metallic magnesium. Preferably, the halogenated hydrocarbon is used in an amount of 1 to 2 moles per gram-atom of magnesium.

The magnesium-containing solid reaction represented by the formula R'OMgX wherein R' and X are defined heretofore product is desirably separated and, if desired, it may be washed with an inert hydrocarbon.

In accordance with an aspect of this invention, the magnesium-containing solid is contacted with the titanium compound and the electron donor compound to form the catalyst component.

Titanium tetrahalides, especially titanium tetrachloride, are suitable as the titanium compound used in the preparation of the catalyst component. Halogen-alcoholates and halogen-phenolates of titanium, such as $Ti(O-n-C_4H_9)_2Cl_2$, $TiOC_2H_5Cl_2$ and $Ti(OC_6H_5)_2Cl_2$, may also be used.

Examples of the electron donor compound used in the preparation of the catalyst component are organic carboxylic acids, organic carboxylic acid esters, alcohols, ethers, ketones, amines, amides, nitriles, aldehydes, alcoholates, compounds of phosphorus, arsenic and antimony bonded to an organic group through carbon or oxygen, phosphoamides, thioethers, thioesters and carbonic acid esters. Of these, the organic acid esters are preferred.

The organic acid esters are esters formed by the condensation of saturated or unsaturated aliphatic, alicyclic and aromatic mono- or polycarboxylic acids with aliphatic, alicyclic and araliphatic mono- or polyols. More specifically, they include, for example, butyl formate, ethyl acetate, butyl acetate, ethyl acrylate, ethyl butyrate, isobutyl isobutyrate, methyl methacrylate, diethyl maleate, diethyl tartrate, ethyl hexahydrobenzoate, ethyl benzoate, ethyl p-methoxybenzoate, methyl p-methylbenzoate, ethyl p-tert.-butylbenzoate, dibutyl phthalate, diallyl phthalate and ethyl alpha-naphthoate. However, the esters are not limited thereto. Of these, the alkyl esters of aromatic carboxylic acids, especially the $C_1$-$C_8$ alkyl esters of benzoic acid or ring-substituted benzoic acids such as p-methylbenzoic acid and p-methoxybenzoic acid, are preferably used.

There can also be used compounds capable of producing in situ the organic acid esters such as alkyl esters of aromatic carboxylic acids which are among the aforesaid electron donor compounds. Benzoyl chloride, benzoic anhydride and phthalic anhydride are illustrative of compounds which can produce the organic acid esters.

The method of contacting the aforesaid magnesium-containing solid, the titanium compound and the electron donor compound may be carried out by various combinations. For example, the compounds may be contacted simultaneously; or any two of these may be first contacted with each other, and then with the remaining one.

The proportions of the substances used are desirably such that the electron donor compound is used in an amount of not more than 1 mole, especially 0.1 to 0.3 mole, per gram-atom of magnesium in the magnesium-containing solid, and also in an amount of 0.2 to 2 moles, preferably 0.5 to 1.5 moles per mole of the titanium compound.

The contacting condition of the aforesaid magnesium-containing solid, the titanium compound and the electron donor compound, whether they are contacted simultaneously or separately, is desirable under heating, for example, at a temperature in the range of 50° to 200° C., for 0.5 to 5 hours. In the case of the contacting of the aforesaid magnesium-containing solid and the electron donor compound, it is desirable to carry out in the presence of the same inert hydrocarbon as described hereinabove with regard to metallic magnesium.

The aforesaid contact treatment can also be carried out in the presence of a halogen compound. Of course, the halogen compound may be so present not only in the case of simultaneous treatment but also in the case of separate treatment. Examples of the halogen compound are silicon halides such as silicon tetrachloride, halogenated aluminum compounds such as aluminum trichloride, dialkyl aluminum monochlorides and alkyl aluminum dichlorides, benzoyl chloride, boron trichloride, phosphorus trichloride, organic halogen compounds shown below and halogen-containing compounds of elements of Group IVa of the periodic table other than carbon. Typical organic halogen compounds are mono- or polyhalogenated compounds of saturated and unsaturated aliphatic, alicyclic and aromatic hydrocarbons. More specifically, examples of the aliphatic compounds are methyl chloride, methyl bromide, methyl iodide, methylene chloride, methylene bromide, methylene iodide, chloroform, bromoform, iodoform, carbon tetrachloride, carbon tetrabromide, carbon tetraiodide, ethyl chloride, ethyl bromide, ethyl iodide, 1,2-dichloroethane, 1,2-dibromoethane, 1,2-diiodoethane, methyl chloroform, methyl bromoform, methyl iodoform, 1,1,2-trichloroethylene, 1,1,2-tribromoethylene, 1,1,2,2-tetrachloroethylene, pentachloroethane, hexachloroethane, hexabromoethane, n-propyl chloride, 1,2-dichloropropane, hexachloropropylene, octachloropropane, decabromobutane and chlorinated paraffin; examples of the alicyclic compounds are chlorocyclopropane, tetrachlorocyclopentane, hexachloropentadiene and hexachlorocyclohexane; and examples of the aromatic compounds are chlorobenzene, bromobenzene, o-dichlorobenzene, p-cyclobenzene, hexachlorobenzene, hexabromobenzene, benzotrichloride and p-chlorobenzotrichloride. In addition to these halo-substituted hydrocarbons, halo-substituted oxygen-containing compounds, such as hexachloroacetone, chloroacetic acid esters and trichloroacetic acid esters, may also be used.

Examples of the halogen-containing compounds of elements of Group IVa of the Periodic Table other than carbon include halogen compounds of silicon, germanium, tin and lead, or the homologs thereof, or other halogen compounds.

Typical halogen-containing compounds of silicon are expressed by the general formula $Si_qX_{2q+2}$ (X is a halogen atom and q is usually an integer of 1 to 10). Specifically, they are polyhalosilanes such as tetrahalosilanes, hexahalodisilanes, octahalotrisilanes, decahalotetrasilanes, dodecahalopentasilanes, tetradecahalohexasilanes and docosahalodecasilanes. In these polyhalosilanes, the halosilane atoms may be identical or different. Of these, preferred compounds are tetrahalosilanes corresponding to m=1. Examples of the tetrahalosilanes are tetrachlorosilane, tetrabromosilane, tetraiodosilane, trichlorobromosilane, trichloroiodosilane, trichlorofluorosilane, dichlorodibromosilane, dichloroiodosilane, chlorotribromosilane, chlorotriiodosilane and tribromoiodosilane. Tetrachlorosilane is readily available commercially and more preferred.

The halogens in the aforesaid halosilane homologs may be partly substituted by one or a plurality of alkyl, aryl, aralkyl, vinyl, alkoxy and acyl groups.

Typical halogen compounds of germanium are expressed by $GeX_n$ wherein X is halogen and n represents an integer of 2 or 4. Specific examples are $GeCl_2$, $GeBr_2$, $GeI_2$, $GeCl_4$, $GeBr_4$ and $GeI_4$. Of these, $GeCl_2$ and $GeCl_4$ are preferred.

The halogens of the above halo-germanium compounds may be partly replaced by one or a plurality of alkyl, aryl, aralkyl, vinyl, alkoxy and acyl groups.

Typical halogen compounds of tin are represented by $SnX_n$ wherein X and n are the same as above. Specific examples include $SnCl_2$, $SnBr_2$, $SnI_2$, $SnCl_4$, $SnBr_4$, $SnI_4$, $SnCl_2Br$, $SnCl_2Br_2$, $SnBr_3Cl$, $SnBr_2I_2$ and $SnCl_2I_2$. Of these, $SnCl_2$ and $SnCl_4$ are preferred. The halogens in the above halo-tin compounds may be substituted by one or a plurality of alkyl, aryl, aralkyl, vinyl, alkoxy and acyl groups.

Typical halogen compounds of lead are represented by $PbX_n$ wherein X and n are the same as above, and specific examples are $PbCl_2$, $PbCl_4$, $PbBr_2$, $PbBr_4$, $PbI_2$ and $PbI_4$. Of these, $PbCl_2$ and $PbCl_4$ are preferred. The halogens of the aforesaid halo-lead compounds may be partly substituted by one or a plurality of alkyl, aryl, aralkyl, vinyl, alkoxy and acyl groups. These various halogen compounds may be used singly or as a combination of two or more.

By this contacting treatment, the magnesium-containing solid changes substantially to magnesium dihalide, and a catalyst component results which has this solid as a carrier and includes the titanium compound and the electron donor compound.

The catalyst component obtained by the method of this invention has a particle diameter of 3 to 30 microns ($\mu$), and such a particle size distribution that particles having a size of 10 to 20$\mu$ constitute at least 70% of all the particles.

The separated catalyst component of this invention may further be contacted with the halogen compound cited above.

Furthermore, the catalyst component obtained as above may be subjected to contacting treatment with a mixture of an organoaluminum compound and an electron donor compound.

The organoaluminum compound used together with the electron donor compound is represented by the general formula $R''_gAlX''_{3-g}$ wherein $R''$ represents an alkyl or aryl group, $X''$ represents a halogen atom, an alkoxy group or a hydrogen atom and g is any number in the range of $1 \leq g \leq 3$). Especially preferred are alkyl aluminum compounds having 1 to 18 carbon atoms, preferably 2 to 6 carbon atoms, such as trialkyl aluminums, dialkyl aluminum monohalides, monoalkyl aluminum dihalides, alkyl aluminum sesquihalides, dialkyl aluminum monoalkoxides and dialkyl aluminum monohydrides; or the mixtures or complexes thereof. Illustrative examples of the trialkyl aluminums are trimethyl aluminum, triethyl aluminum, tripropyl aluminum, triisobutyl aluminum and trihexyl aluminum; examples of the dialkyl aluminum monohalides are dimethyl aluminum chloride, diethyl aluminum chloride, diethyl aluminum bromide, diethyl aluminum iodide and diisobutyl aluminum chloride; examples of the monoalkyl aluminum dihalides are methyl aluminum dichloride, ethyl aluminum dichloride, ethyl aluminum dibromide, ethyl aluminum diiodide and isobutyl aluminum dichloride; an example of the alkyl aluminum sesquihalide is ethyl aluminum sesquichloride; examples of the dialkyl aluminum monoalkoxides are dimethyl aluminum ethoxide, diethyl aluminum ethoxide, diethyl aluminum phenoxide, dipropyl aluminum ethoxide, diisobutyl aluminum ethoxide and diisobutyl aluminum phenoxide; and examples of the dialkyl aluminum hydrides are dimethyl aluminum hydride, diethyl aluminum hydride, dipropyl aluminum hydride and diisobutyl aluminum hydride.

The electron donor compound to be used with these organoaluminum compounds may be properly selected from the compounds exemplified hereinabove.

The catalyst component so obtained exhibits an outstanding effect in that when combined with an organoaluminum compound, exhibits high activity and high stereospecificity in the homopolymerization of an alpha-olefin or the copolymerization of it with ethylene or another alpha-olefin, and that polymers obtained therein have a very narrow particle size distribution and are semi-transparent particles having unique particle characteristics not seen with conventional supported catalysts.

The organoaluminum compounds used in combination with the catalyst component in the polymerization of alpha-olefins may be properly selected from the organoaluminum compounds described hereinabove. Of these, trialkyl aluminums are especially desirable, and triethyl aluminum and triisobutyl aluminum can be cited as examples thereof. Furthermore, these trialkyl aluminums may be used in combination with other organoaluminum compounds. Specific examples thereof are diethyl aluminum chloride, ethyl aluminum dichloride, ethyl aluminum sesquichloride, diethyl aluminum ethoxide and diethyl aluminum hydride, or the mixtures or complexes thereof. They are desirable because they are readily available commercially and exhibit excellent effects.

The amount of the organoaluminum compound to the catalyst component is usually 1 to 2,000 moles, desirably 50 to 500 moles, per gram-atom of titanium in the catalyst component.

Preferably, the organoaluminum compound is used in combination with the aforesaid electron donor compound used in the preparation of the catalyst component. Among the aforesaid electron donor compounds, organic acid esters can be cited as desirable electron donor compounds. Among them, aromatic carboxylic acid esters, especially the $C_1$–$C_8$ alkyl esters of benzoic acid and ring-substituted benzoic acids such as p-methoxybenzoic acid or p-methylbenzoic acid are preferred.

The ratio between the organoaluminum compound and the electron donor compound in this case is selected such that the proportion of the organoaluminum compound is in the range of 0.1 to 10, preferably 1 to 5, gram atoms as aluminum per mole of the electron donor compound.

The present invention is directed to the polymerization of olefins using a catalyst composed of the catalyst component obtained as above and the organoaluminum compound (and the electron donor compound). Particularly, it can be used in the stereospecific polymerization of alpha-olefins having 3 to 6 carbon atoms such as propylene, butene-1, 4-methylpentene-1 and hexene-1, and the copolymerization of the aforesaid alpha-olefins with each other and/or with ethylene. The copolymerization includes both random and block copolymerizations. When ethylene is used as a comonomer, its amount is usually up to 30% by weight, particularly 1 to 15% by weight, based on the alpha-olefin. The conditions under which polymerization is carried out with the catalyst system of this invention are the same as those well known in the art.

The reaction may be carried out in the gaseous or liquid phase. The liquid-phase reaction may be performed either in an inert hydrocarbon or liquid monomer. When the polymerization is carried out in solvent, suitable solvents are selected from the aforesaid inert hydrocarbons. The polymerization temperature is usually from $-80°$ C. to $150°$ C., preferably from $40°$ C. to $100°$ C. The pressure can, for example, be from 1 to 40 atmospheres. The control of the molecular weight of the polymer during the polymerization is carried out by known methods which involve the presence of hydrogen or other known molecular weight controlling agents. The method of polymerization may either be continuous or batchwise.

When an alpha-olefin is polymerized by the process of this invention, both the polymerization activity and stereospecificity of the catalyst are high. Accordingly, both a step of removing the catalyst and a step of removing atactic polymer become unnecessary, or at least loads can be markedly reduced. Furthermore, the polymer obtained by the process of this invention exhibits a uniform particle size distribution within a narrow range, and has a large particle diameter with a low content of fine powder, and, therefore, has good free-flowability. Hence, the aforesaid effects are outstanding. In addition, the resulting polymer exhibits the unique property of being semi-transparent, which is not seen with conventional supported catalysts.

The process of this invention is especially important for the production of isotactic polypropylene, a random copolymer of ethylene and propylene, and a block copolymer of ethylene and propylene.

The following Examples specifically illustrate the present invention. The invention, however, is not intended to be limited by these examples alone. All percentages (%) shown in the examples are by weight unless otherwise specified. The polymerization activity Kc is the amount (g) of polymer formed per gram of catalyst. Kt is the amount (kg) of polymer per gram of Ti. The heptane-insoluble portion (to be abbreviated as H.I. hereinbelow), which shows the proportion of crystalline polymer in the resulting polymer, denotes the residual amount of polymer when it is extracted for 6 hours with boiling n-heptane in a modified Soxhlet extractor. The melt flow rate (MFR) was measured in accordance with ASTM-D1238.

EXAMPLE 1

Preparation of a Magnesium-Containing Solid

A 1-liter reactor equipped with a reflux condenser was charged under an atmosphere of nitrogen gas with 12.8 g (0.53 mole) of chips of metallic magnesium (purity 99.5%, average particle diameter 1.6 mm) and 250 ml of n-hexane. They were stirred for 1 hour at 68° C., and the magnesium metal was taken out and dried under reduced pressure at 65° C. to obtain preactivated metallic magnesium.

To the resulting metallic magnesium were added 88 ml (0.53 mole) of ethyl ortho-formate and as a promoter, 0.5 ml of a 10% by weight methyl iodide solution of iodine. The resulting suspension was maintained at 55° C., and 5 ml of a solution of 80 ml (0.8 mole) of n-butyl chloride in 100 ml of n-hexane was added dropwise, and after stirring the mixture for 50 minutes, the remainder of the solution was added dropwise over the course of 80 minutes. With stirring, the reaction was performed at 70° C. for 4 hours to afford a solid reaction product.

The reaction product was washed six times at 50° C. with 300 ml of n-hexane and dried under reduced pressure at 60° C. for 1 hour to recover 55.6 g of a magnesium-containing solid. The solid contained 22.5% of magnesium, and 34.0% of chlorine.

Preparation of a Catalyst Component

A 300 ml reactor equipped with a reflux condenser was charged under an atmosphere of nitrogen gas with 13.5 g of the resulting magnesium-containing solid, 200 ml of n-hexane and 4.32 ml (41.5 millimoles; 0.33 mole per gram-atom of magnesium in the magnesium-containing solid) of benzoyl chloride to form a suspension. They were contacted and reacted at 70° C. for 2 hours, and then the solid substance was washed three times at 65° C. with 150 ml of n-hexane.

150 ml of titanium tetrachloride was added to the washed solid substance, and the contacting treatment was performed at 120° C. for 2 hours. The product was hot-filtered at 120° C., washed 10 times at 65° C. with 150 ml of n-hexane and dried under reduced pressure at 50° C. for 1 hour to obtain 11.5 g of a catalyst component of this invention having the following composition (Ti 2.3% by weight, Mg 19.8% by weight, Cl 67.1% by weight). The particle size distribution of this catalyst component was as follows:

26 microns or more: 0.1% by weight
20 microns or more: 21.7% by weight
10 microns or more: 70.5% by weight
5 microns or more: 6.0% by weight
less than 5 microns: 1.8% by weight

Polymerization of Propylene 76.4 mg of the aforesaid catalyst component, 11.0 ml (corresponding to 300 gram-atoms as aluminum per gram of titanium in the catalyst component) of an n-heptane solution containing 1 mole, per liter of n-heptane, of triethyl aluminum (to be abbreviated as TEAL hereinbelow), and 0.46 ml (corresponding to 0.29 mole per gram-atom of aluminum in the TEAL) of ethyl p-methoxybenzoate were mixed, and maintained for 5 minutes. The mixture was charged into a 1-liter stainless steel (SUS 32) autoclave equipped with a stirrer under an atmosphere of nitrogen gas. Then, 0.6 liter of hydrogen gas as a molecular weight controlling agent and 0.8 liter of liquified propylene were introduced under pressure into the autoclave. The reaction system was then heated to 68° C., and propylene was polymerized for 30 minutes. After the polymerization, the unreacted propylene was purged to obtain 221 g of polypropylene as a white powder.

The polymerization activity Kc was 2900, and Kt was 126. Furthermore, HI was 95.5% and MFR was 3.2.

The polymer was semi-transparent, and had a bulk density of 0.51 g/cm³. It had the following particle size distribution:

840 microns or more: 0.5% by weight
590 microns or more: 21.4% by weight
420 microns or more: 47.8% by weight
350 microns or more: 20.1% by weight
250 microns or more: 8.0% by weight
149 microns or more: 2.0% by weight
53 microns or more: 0.2% by weight
less than 53 microns: 0% by weight

EXAMPLES 2 AND 3

A catalyst component was prepared in the same way as in Example 1 except that in the preparation of the magnesium-containing solid in Example 1, the reaction after the dropwise addition of the n-hexane solution of n-butyl chloride was performed at each of the temperatures shown in Table 1 instead of performing it at 70° C. for 4 hours. Propylene was polymerized in the same way as in Example 1 using the resulting catalyst component. The results are shown in Table 1.

TABLE 1

| Example | Temperature (°C.) | Time (hours) | Kc | Kt | HI (%) | MFR | Bulk density (g/cm³) |
| --- | --- | --- | --- | --- | --- | --- | --- |
| 2 | 50 | 4 | 3050 | 130 | 93.9 | 4.8 | 0.49 |
| 3 | 90 | 4 | 2790 | 123 | 95.6 | 2.5 | 0.48 |

EXAMPLE 4

A catalyst component was prepared in the same way as in Example 1 except that in the preparation of the magnesium-containing solid in Example 1, two molar times of ethyl ortho-formate was used instead of using it in an amount equimolar to metallic magnesium. Propylene was polymerized in the same way as in Example 1 using the resulting catalyst component. The results were: Kc 3100, Kt 150, HI 92.9%, MFR 6.0, bulk density 0.50 g/cm³.

EXAMPLES 5 TO 7

A catalyst was prepared in the same way as in Example 1 except that in the preparation of the magnesium-containing solid in Example 1, each of the compounds indicated in Table 2 was used instead of ethyl orthoformate. Propylene was polymerized in the same way as in Example 1 using the resulting catalyst component. The results are shown in Table 2.

TABLE 2

| Example | Alkoxy compound | Kc | Kt | HI (%) | MFR | Bulk density (g/cm³) |
| --- | --- | --- | --- | --- | --- | --- |
| 5 | Methyl ortho-formate | 4500 | 290 | 90.8 | 7.2 | 0.47 |
| 6 | Ethylidene diethyl ether | 1900 | 86 | 94.5 | 6.0 | 0.49 |
| 7 | Ethyl ortho-carbonate | 1810 | 59 | 96.1 | 4.9 | 0.48 |

EXAMPLES 8 TO 10

A catalyst component was prepared in the same way as in Example 1 except that in the preparation of the catalyst component in Example 1, the benzoyl chloride was used in the amounts shown in Table 3. Propylene was polymerized in the same way as in Example 1 using the resulting catalyst component. The results are shown in Table 3.

TABLE 3

| Example | PhCOCl/Mg (mole ratio) | Kc | Kt | HI (%) | MFR | Bulk density (g/cm$^3$) |
|---|---|---|---|---|---|---|
| 8 | 0.02 | 3150 | 152 | 94.3 | 2.5 | 0.50 |
| 9 | 1 | 2050 | 105 | 95.0 | 4.0 | 0.49 |
| 10 | 2 | 2100 | 110 | 94.9 | 3.0 | 0.47 |

EXAMPLE 11

Preparation of a Magnesium-Containing Solid

A one-liter reactor equipped with a reflux condenser was charged with 0.5 mole of n-butyl magnesium chloride and 200 ml of toluene. The reaction solution was maintained at 50° C., and a mixed solution of 146 g (0.3 mole) of phenyl ortho-formate and 100 ml of toluene was added dropwise over the course of 50 minutes. Then, with stirring, the reaction was performed at 70° C. for 4 hours to afford a solid reaction product. The reaction product was treated in the same way as in Example 1 to recover 60.1 g of a magnesium-containing solid. The solid contained 21.3% of magnesium and 30.9% of chlorine.

Preparation of a Catalyst Component

The contacting treatment with titanium tetrachloride was performed in the same way as in Example 1 except that after treating the magnesium-containing solid with benzoyl chloride in Example 1, ethyl benzoate was used in an equimolar amount to 1 gram-atom of magnesium in the magnesium-containing solid. Thus, a catalyst component was obtained.

Polymerization of Propylene

Propylene was polymerized in the same way as in Example 1. The results were as follows: Kc 2050, Kt 103, HI 89.5%, MFR 4.0, bulk density 0.46 g/cm$^3$.

EXAMPLES 12 AND 13

A catalyst component was prepared in the same way as in Example 11 except that each of the compounds shown in Table 4 was used instead of the phenyl ortho-formate used in the preparation of the magnesium-containing solid in Example 11. Propylene was polymerized in the same way as Example 1 using the resulting catalyst component. The results are shown in Table 4.

TABLE 4

| Example | Alkoxy compound | Kc | Kt | HI (%) | MFR | Bulk density (g/cm$^3$) |
|---|---|---|---|---|---|---|
| 12 | Ethylidene diethyl ether | 1750 | 95 | 93.0 | 3.5 | 0.48 |
| 13 | Ethyl ortho-carbonate | 1800 | 73 | 92.5 | 5.2 | 0.47 |

EXAMPLE 14

Preparation of a Catalyst Component

A 300 ml reactor equipped with a reflux condenser was charged under an atmosphere of nitrogen gas with 4.6 g of the resulting magnesium-containing solid prepared as in Example 1, 120 ml of n-hexane and 1.7 g (7.5 millimoles, 0.2 mole per gram-atom of magnesium in the magnesium-containing solid) of benzoic anhydride to form a suspension.

They were contacted and reacted at 70° C. for 2 hours, and then the solid substance was washed three times with 150 ml of n-hexane at 65° C. each time.

Then, 150 ml of titanium tetrachloride was added, and the contacting treatment was performed at 120° C. for 2 hours. The solid substance was hot-filtered at 120° C., washed 10 times with 150 ml of n-hexane at 65° C. each time, and dried under reduced pressure at 50° C. for 1 hour to obtain 4.1 g of a catalyst component of this invention having the following composition (Ti 2.5% by weight).

Polymerization of Propylene

Propylene was polymerized in the same manner as in Example 1 using 75.4 mg of the aforesaid catalyst component to obtain 245 g of polypropylene. The polymerization activity Kc was 3250, and Kt was 130. Furthermore, HI was 93.5%, MFR was 4.4, and bulk density was 0.50 g/cm$^3$.

EXAMPLE 15

Preparation of a Catalyst Component

A catalyst component was prepared in the same manner as in Example 14 using 10.9 g of magnesium-containing solid prepared as in Example 1, 130 ml of n-hexane and 3.9 g (31.9 millimoles; 0.33 mole per gram-atom of magnesium in the magnesium-containing solid) of benzoic acid (Ti 2.9% by weight).

Polymerization of Propylene

Propylene was polymerized in the same was as in Example 1 using 59.7 mg of the aforesaid catalyst component to obtain 137 g of polypropylene. The polymerization activity Kc was 2300, and Kt was 79. Furthermore, HI was 93.5%, MFR was 4.0 and bulk density was 0.48 g/cm$^3$.

EXAMPLE 16

Preparation of a Catalyst Component

A catalyst component was prepared in the same manner as in Example 14 using 6.7 g of magnesium-containing solid prepared as in Example 1, 130 ml of n-hexane and 2.8 ml (19.6 millimoles; 0.33 mole per gram-atom of magnesium in the magnesium-containing solid) of ethyl benzoate (Ti 3.7% by weight).

Polymerization of Propylene

Propylene was polymerized in the same manner as in Example 1 using 81.6 mg of the aforesaid catalyst component to obtain 125 g of polypropylene.

The polymerization activity Kc was 1530 and Kt was 41. Furthermore, HI was 92.1%, MFR was 5.5 and bulk density was 0.48 g/cm$^3$.

What is claimed is:

1. A supported titanium-containing catalyst component obtained by contacting at a temperature in the range of about 50° to 200° C. (1) a magnesium-containing solid represented by the formula R'OMgX, said magnesium-containing solid obtained by reacting (a) magnesium metal, (b) a halogenated hydrocarbon represented by the formular RX wherein R can be an alkyl, aryl or cycloalkyl group having 1 to about 20 carbon atoms and X is a halogen atom, and (c) a compound represented by the formula $X'_mC(OR')_{4-m}$ wherein X' can be a hydrogen atom, a halogen atom, an alkyl, aryl, cycloalkyl group having from 1 to about 10 carbon atoms or a halogenated alkyl, aryl or cycloalkyl group, R' can be an alkyl or cycloalkyl group having from 1 to about 20 carbon atoms and m is 0, 1 or 2, (2) a titanium compound and (3) one of an electron donor or a compound capable of producing in situ an organic carboxylic acid ester.

2. The catalyst component of claim 1 wherein the contacting is performed in the presence of an inert hydrocarbon.

3. The catalyst component of claim 1 wherein the contacting is performed simultaneously.

4. The catalyst component of claim 1 wherein the magnesium-containing solid is contacted with a compound capable of producing an organic acid ester in situ and thereafter contacted with a titanium compound.

5. The catalyst component of claim 4 wherein the compound capable of producing an organic acid ester is benzoyl chloride and the titanium compound is titanium tetrachloride.

6. A catalyst system comprising the supported titanium catalyst component of claim 1 and an organoaluminum co-catalyst.

7. A catalyst system comprising the supported titanium catalyst component of claim 2 and an organoaluminum co-catalyst.

8. A catalyst system comprising the supported titanium catalyst component of claim 3 and an organoaluminum co-catalyst.

9. A catalyst system comprising the supported titanium catalyst component of claim 4 and an organoaluminum co-catalyst.

10. A catalyst system comprising the supported titanium catalyst component of claim 5 and an organoaluminum co-catalyst.

11. A process for the preparation of a supported titanium-containing catalyst component, said process comprising contacting at a temperature in the range of about 50° to 200° C. (1) a magnesium-containing solid represented by the formula R'OMgX, said magnesium-containing solid obtained by reacting (a) magnesium metal, (b) a halogenated hydrocarbon represented by the formula RX wherein R can be an alkyl, aryl or cycloalkyl group having 1 to about 20 carbon atoms and X is a halogen atom; and (c) a compound represented by the formula $X'_mC(OR')_{4-m}$ wherein X' can be a hydrogen atom, a halogen atom, an alkyl, aryl, cycloalkyl group having from 1 to about 10 carbon atoms or a halogenated alkyl, aryl or cycloalkyl group, R' can be an alkyl, aryl or cycloalkyl group having from 1 to about 20 carbon atoms and m is 0, 1 or 2, (2) a titanium compound and (3) one of an electron donor or a compound capable of producing in situ an organic carboxylic acid ester, and recovering the supported titanium-containing catalyst.

12. The process of claim 11 wherein the contacting is performed in the presence of an inert hydrocarbon.

13. The process of claim 11 wherein the contacting is performed simultaneously.

14. The process of claim 11 wherein the magnesium-containing solid is contacted with a compound capable of producing an organic carboxylic acid ester in situ and thereafter contacted with a titanium compound.

* * * * *